United States Patent [19]

Schneberger et al.

[11] Patent Number: 5,242,422
[45] Date of Patent: Sep. 7, 1993

[54] ONE PIECE MOLDED SYRINGE WITH TETHERED CAP

[75] Inventors: Gary E. Schneberger; Barry L. Snyder, both of Ocala, Fla.; Nancy J. Voiselle, Greenwood, S.C.

[73] Assignee: Professional Medical Products, Inc., Greenwood, S.C.

[21] Appl. No.: 800,036

[22] Filed: Nov. 29, 1991

[51] Int. Cl.⁵ ........................................... A61M 5/178
[52] U.S. Cl. ................................. 604/216; 604/212; 604/263; 222/206
[58] Field of Search ............... 604/212, 216, 217, 905, 604/185, 187, 192, 263; 222/92, 95, 107, 215, 541, 572, 206, 210

[56] References Cited

U.S. PATENT DOCUMENTS

| | | | |
|---|---|---|---|
| 2,155,759 | 4/1939 | Hocke | 222/92 |
| 2,194,658 | 3/1940 | Hirst | 222/92 |
| 2,747,574 | 5/1956 | De Lorenzo . | |
| 2,809,771 | 10/1957 | Ward . | |
| 2,837,822 | 6/1958 | Wille . | |
| 2,864,367 | 12/1958 | Mende . | |
| 2,869,545 | 1/1959 | Forsyth . | |
| 2,925,935 | 2/1960 | Nomura | 222/92 |
| 3,083,877 | 4/1963 | Gash . | |
| 3,154,074 | 10/1964 | Harrison . | |
| 3,303,847 | 2/1967 | Eaton . | |
| 3,595,441 | 7/1971 | Grosjean | 222/107 |
| 3,658,061 | 4/1972 | Hall . | |
| 3,705,584 | 12/1972 | Fript | 604/212 |
| 3,802,435 | 4/1974 | Claasen . | |
| 3,826,409 | 7/1974 | Chilcoate . | |
| 3,938,514 | 2/1976 | Boucher | 222/206 X |
| 4,112,942 | 9/1978 | Scaife . | |
| 4,410,323 | 10/1983 | Hodosh et al. . | |
| 4,411,656 | 10/1983 | Cornett, III | 604/212 |
| 4,610,667 | 9/1986 | Pedicano et al. . | |
| 4,623,336 | 11/1986 | Pedicano et al. . | |
| 4,752,288 | 6/1988 | Hussey . | |
| 4,753,638 | 6/1988 | Peters . | |
| 4,867,746 | 9/1989 | Dufresne . | |
| 4,883,469 | 11/1989 | Glazier . | |
| 4,898,295 | 2/1990 | Kim | 220/66 |
| 4,932,947 | 6/1990 | Cardwell . | |
| 4,955,866 | 9/1990 | Corey . | |

FOREIGN PATENT DOCUMENTS

| | | | |
|---|---|---|---|
| 156635 | 11/1969 | Fed. Rep. of Germany | 604/212 |
| 640599 | 5/1962 | Italy | 604/212 |
| 1621946 | 1/1991 | U.S.S.R. | 604/212 |
| 8701944 | 4/1987 | World Int. Prop. O. | 604/212 |

Primary Examiner—C. Fred Rosenbaum
Assistant Examiner—Corrine Maglione
Attorney, Agent, or Firm—Bell, Seltzer, Park & Gibson

[57] ABSTRACT

A one-piece molded syringe with tethered cap is disclosed. The syringe has a hollow body having two parts, a pleated part forming a substantial part of the hollow body and a forward portion connected to the pleated part having a reduced cross-sectional area for receiving the fingers of a user. The cap is tethered to the syringe for maintaining the accessibility of the cap. A projection or pair of projections, formed integrally with the forward portion of the syringe, have a frusto-conical shape to receive the cap thereon. The projection(s) extends laterally outward from the forward portion to also serve as an abutment to prevent the syringe from rolling along a surface.

17 Claims, 2 Drawing Sheets

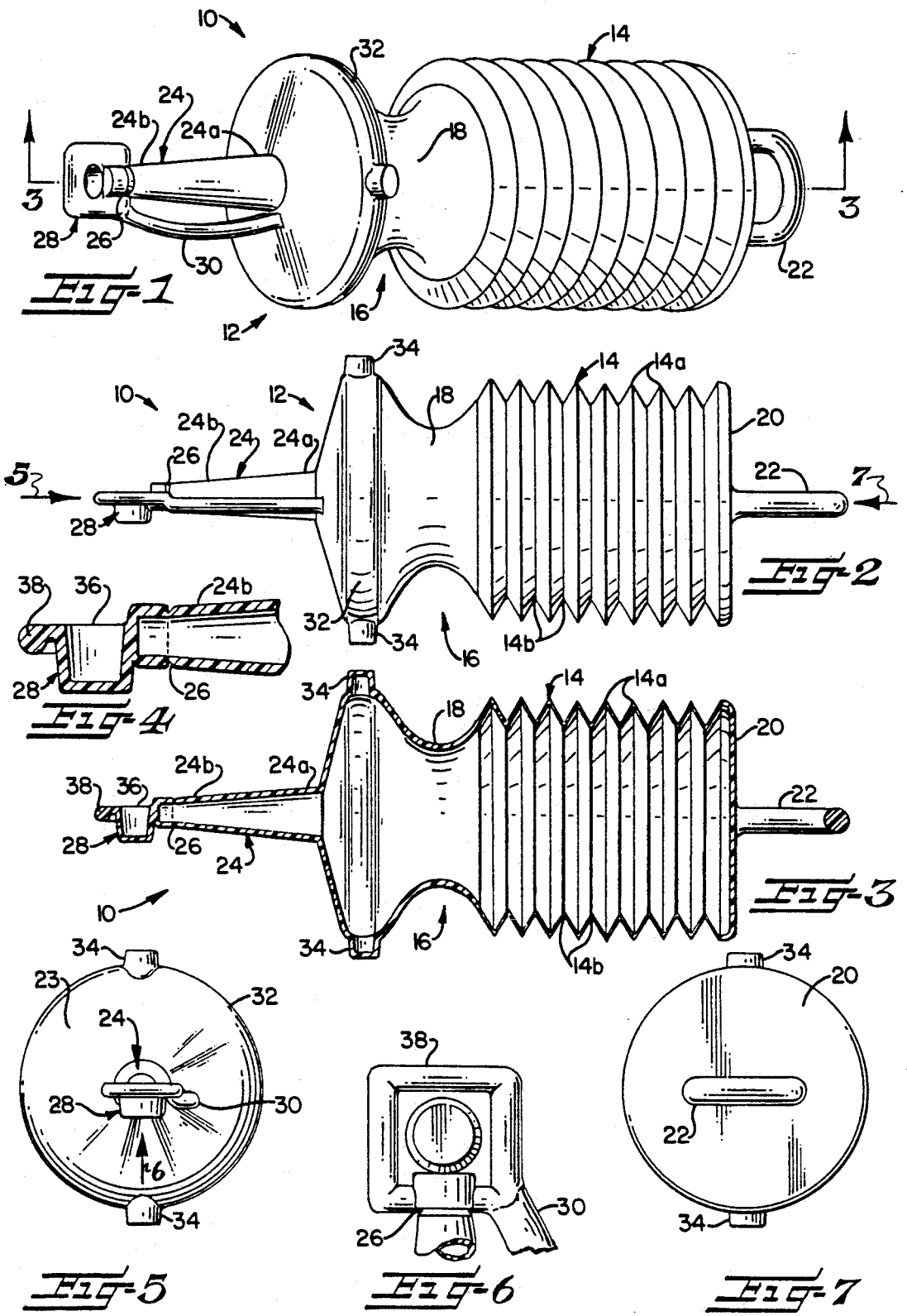

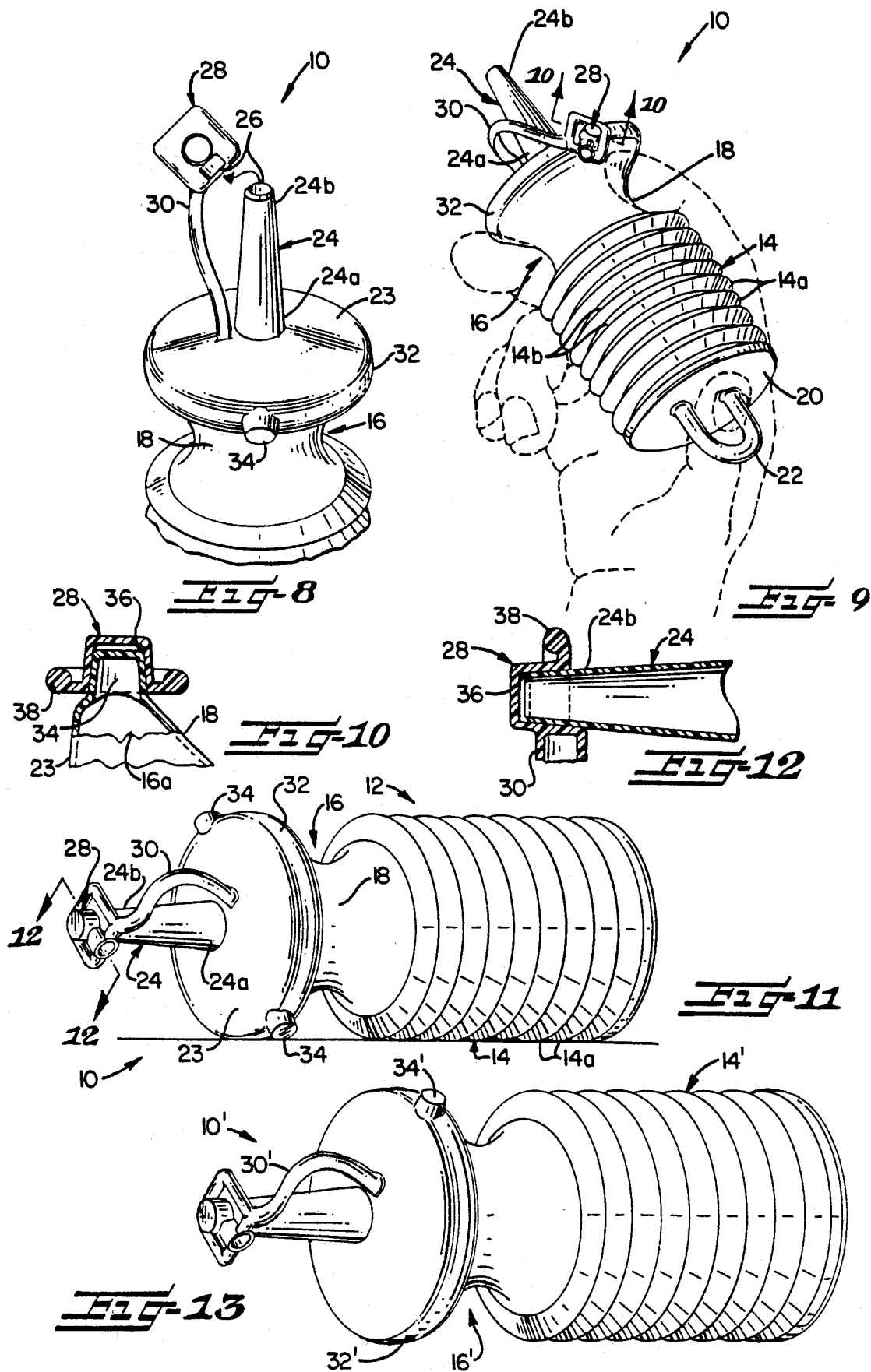

ONE PIECE MOLDED SYRINGE WITH TETHERED CAP

FIELD OF THE INVENTION

The invention relates to prefilled, molded syringes and more particularly to one piece prefilled molded syringes.

BACKGROUND OF THE INVENTION

Molded syringes are generally known in the art of medical science. These syringes may be used in both sterile and non-sterile environments. Typical uses include bladder irrigation, wound irrigation, as well as other body irrigation. Molded syringes may also be used for dispensing liquids including sterile water, saline, hydrogen peroxide, nutritive liquids, stool softeners (enemas), douche products and the like.

When used in sterile environments, it is essential that the sterility of the syringe and the fluid displaced within the syringe be maintained at all times, including during manufacture of the syringe, filling of the syringe, storage of the filled syringe, use of the syringe and even after use in the event it is reusable.

A one-piece disposable fluid-filled syringe is described in U.S. Pat. No. 4,411,656 to Cornett. Cornett discloses a one-piece prefilled syringe. The syringe of Cornett also has a cap which can be removably placed over the tip of the syringe between uses to maintain the sterility of the contents of the syringe.

Caps are also used with hypodermic needles to prevent a needle from accidentally contacting a person and resulting in infection or puncture like wounds. Caps for hypodermic needles are described in U.S. Pat. Nos. 4,883,469 to Glazier; 3,658,061 to Hall, 4,867,746 to Dufresne; 4,955,866 to Corey; and 4,610,667 and 4,623,336 to Pedicano et al.

It would be desirable to have a molded syringe which readily provides for closing the syringe and ensures the sterility of its contents during manufacture including filling, storage, use and between successive uses of the syringe.

SUMMARY OF THE INVENTION

It is therefore an object of the present invention to provide a one piece molded syringe which readily provides for closing the syringe after use and ensures the sterility of the fluid contained therein during manufacture including filling, use and storage between successive uses.

It is another object of the present invention to provide a one piece molded syringe with a cap that may be easily removed from and placed on the nozzle of the syringe and means for preventing loss or dislocation of the cap.

It is a further object of the present invention to provide a one piece molded syringe having means for receiving a cap for the syringe and for preventing contamination of the contents of the syringe resulting from contact of the syringe tip and/or contents of the syringe with other objects.

These and other objects are provided, according to the present invention, by a one piece molded syringe having a reuseable closure cap connected to the hollow body of the syringe. The syringe is disposable and may be used one or more times depending on the desired application. The syringe has a hollow body having two portions, a pleated (bellowed) portion forming a substantial part of the hollow body and a forward portion adjoining the pleated portion. The pleated portion has a closed rear wall while the forward portion has a reduced cross sectional area permitting the user of the syringe to grip the area with his/her fingers during use. A ring (prehensile attachment) is formed integrally with the closed rear wall of the hollow body. The ring receives the user's thumb during use and permits the user to handle the syringe by placing the thumb in the thumb ring and the fingers about the reduced cross sectional area of the forward portion of the hollow body. The ring facilitates application of positive or negative pressure to the pleated portion.

The nozzle of the syringe is connected to the forward portion of the hollow body and communicates with the interior of the hollow body. A fracturable closure seal, formed integrally with the outer end of the nozzle during manufacture, seals the nozzle prior to initial use. During use, a user places his/her thumb in the thumb engageable ring and fingers about the reduced cross sectional area of the forward portion of the hollow body. After breaking of the fracturable closure seal formed integrally with the outer end of the nozzle, the contents of the syringe is displaced through the nozzle.

A closure cap is connected to the hollow body, preferably the forward portion of the hollow body, via a tether. While the syringe is in use, the closure cap is placed over a projection extending laterally outward from the forward portion of the hollow body. The laterally outward extending projection is frusto-conically shaped for receiving the closure cap thereon which has an inner mating frusto-conical shape. By placing the closure cap on an outward extending projection, the closure cap does not interfere with the use of the syringe while the contents of the syringe is displaced from the hollow body. The projection also serves as an abutment to prevent the syringe from rolling along a surface.

The tether which connects the closure cap to the hollow body of the syringe prevents dislocation of the closure cap from the hollow body. Thus, the closure cap is always accessible for closing the nozzle after each use of the syringe to prevent leakage or contamination of the contents of the syringe.

Alternatively, the syringe may have more than one projection extending laterally outward from the hollow body of the syringe. In the multiple projection embodiment, it is preferable that the projections be placed on opposite sides of the hollow body. As a result, the closure cap may be placed over either projection while the syringe is in use. In addition, while the syringe is not in use and the closure cap is placed over the outer end of the nozzle to prevent displacement of the contents of the syringe, the projections will also serve as an abutment to prevent rolling of the syringe along a surface.

BRIEF DESCRIPTION OF THE DRAWINGS

FIG. 1 is a perspective view of a one piece molded syringe with tethered cap according to the present invention;

FIG. 2 is a side elevational view thereof rotated 90° from that shown in FIG. 1;

FIG. 3 is a vertical sectional view taken along line 3—3 of FIG. 1;

FIG. 4 is a fragmentary cross-sectional view of the nozzle, fracturable closure seal and closure cap of the present invention;

FIG. 5 is a front elevational view thereof looking in the direction of arrow 5 of FIG. 2;

FIG. 6 is a side elevational view of the closure cap and fracturable closure seal of the syringe looking in the direction of arrow 6 of FIG. 5;

FIG. 7 is a rear elevational view thereof looking in the direction of arrow 7 of FIG. 2;

FIG. 8 is a fragmentary perspective view of the forward portion of the syringe according to the present invention having the fracturable closure seal fractured;

FIG. 9 is a perspective view thereof having the closure cap placed on a laterally outward extending projection;

FIG. 10 is a fragmentary cross-sectional view of the closure cap placed over the laterally outward extending projection of the syringe taken along line 10—10 of FIG. 9;

FIG. 11 is a perspective view of the syringe according to the present invention having the closure cap placed over the outer end of the nozzle;

FIG. 12 is a fragmentary cross-sectional view of the nozzle taken along line 12—12 of FIG. 11; and FIG. 13 is a perspective view of a second embodiment of the syringe according to the present invention.

DESCRIPTION OF A PREFERRED EMBODIMENT

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Referring to FIG. 1, a one piece molded syringe with tethered cap according to the present invention is illustrated generally at 10. Syringe 10 has an elongate hollow body 12 which acts as a reservoir for holding the contents of the syringe. The syringe may contain sterile water, saline, hydrogen peroxide, nutritive liquids, stool softeners (enemas), douche products or potentially any other sterile fluid used for bladder irrigation, wound irrigation or irrigation of other body parts. The size of syringe 10 may vary to accommodate a range in volume as desired.

Elongate hollow body 12 has a longitudinal axis and has two parts or portions, a pleated (bellowed) body part 14 which forms a substantial portion of the hollow body and a finger gripping part (forward portion) 16 which has a reduced cross sectional area 18 for receiving fingers of a user during use. Pleated body part 14 is adjoined on one end by closed rear wall 20 (not shown) and by finger gripping part 16 on the opposite end. Closed rear wall 20 has a thumb ring 22 for receiving or engaging the thumb of a user.

Syringe 10 also has a nozzle 24 which is frusto-conically shaped. The larger end 24a of frusto-conically shaped nozzle 24 is connected to finger-gripping part 16 of syringe 10. The smaller end 24b of frusto-conically shaped nozzle 24 is formed integrally with and adjacent to fracturable closure seal 26 which closes nozzle 24 of syringe 10 until the syringe is initially used. Finally, closure cap 28, formed integrally with fracturable closure seal 26, is connected to the forward portion 16 of syringe 10 by tether 30.

Referring to FIG. 2, a side elevational view of syringe 10 according to the present invention is illustrated. Pleated part 14 of hollow body 12 is formed by a number of pleated (bellowed) sections, each pleated section having an outward portion 14a and an inward portion 14b. As such, pleated part 14 can expand and contract during use by placing a thumb in thumb ring 22 and fingers about finger-gripping part 16 and expanding and contracting pleated part 14. When expanded, outward pleated sections 14a are displaced further apart as are inward pleated sections 14b. When a user contracts pleated part 14 by forcing closed rear wall 20 towards finger-gripping part 16, outward pleated sections 14a are moved closer together as are inward pleated sections 14b, thus causing the contents of hollow body 12 to be forced towards nozzle 24 and through nozzle 24 when nozzle 24 is open. Thus, thumb ring 22 facilitates application of positive or negative pressure to pleated part 14.

Finger-gripping part 16 has a reduced cross sectional area 18 for receiving the fingers of a user about the cross sectional area. Finger-gripping part 16 is attached to the forward end of pleated part 14 and to larger end 24a of nozzle 24. Gripping part 16 has a shielding disk 32 which has a diameter approximately equal to the diameter of outward pleated sections 14a of pleated part 14. Shielding disk 32 is hollow so that the contents of the syringe can pass through the shielding disk and into nozzle 24. It also acts as additional reservoir space to hold the contents of the syringe. Projections 34, having a frusto-conical shape, are formed integrally with shielding disk 32. The projections are hollow and capable of communicating with finger-gripping part 16 of hollow body 12. Thus, projections 34 may also receive a portion of the contents of syringe 10.

Referring to FIG. 3, syringe 10 is formed using a blow molding process which will be described below. Thus, different parts of syringe 10 have a different exterior wall thickness. For example, the exterior walls of outward pleated sections 14a and inward pleated sections 14b are thinner than the exterior wall of finger gripping part 16 and nozzle 24.

Referring to FIG. 4, a cross-sectional view of nozzle 24, fracturable closure seal 26 and closure cap 28 is illustrated. During initial use of syringe 10, fracturable closure seal 26 is broken or fractured to initially open nozzle 24. The interior 36 of closure cap 28 has a mating frusto-conical shape which is capable of being placed over the frusto-conically shaped nozzle 24 to close nozzle 24 once fracturable closure seal 26 has been broken. Cap 28 also has a flange 38 which extends outwardly around the entire perimeter of closure cap 28. Flange 38 facilitates manual grasping of the closure cap to enhance handling of the cap 28, including removal of the cap once displaced over nozzle 24 or projections 34.

Referring to FIG. 5, a front elevational view looking in the direction of arrow 5 of FIG. 2 is illustrated. In particular, projections 34 extend laterally outward from opposite sides of shielding disk 38 of finger gripping part 16. Nozzle 24 is connected to hollow body top 23 of finger gripping part 16 and closure cap 28 by tether 30.

Referring to FIG. 6, closure cap 28 is illustrated looking in the direction of arrow 6 of FIG. 5. Flange 38 of the closure cap extends outwardly surrounding the cap. As previously described, flange 38 enhances manual grasping of closure cap 28. Tether 30 is connected to a corner of flange 38. It will be understood by those having skill in the art that flange 38 could have a shape other than roughly square and that tether 30 may be connected to closure cap 28 at some point other than a corner of flange 38.

Referring to FIG. 7, a rear elevational view looking in the direction of arrow 7 of FIG. 2 is illustrated. Closed rear wall 20 forms the rear-end of pleated part 14 of hollow body 12 to thereby seal the rear-end of hollow body 12. Thumb ring 22 is attached to closed rear wall 20 for receiving or engaging a user's thumb to permit manipulation of syringe 10 during use including application of positive and negative pressure.

Referring to FIG. 8, finger gripping part 16 and nozzle 24 of syringe 10 are illustrated after fracturable closure seal 26 has been broken or fractured. Frusto-conically shaped nozzle 24 having larger end 24a connected to hollow body top 23 of finger gripping part 16, has smaller end 24b extending outwardly therefrom. Fracturable closure seal 26 (see FIGS. 1-4) is integrally formed with nozzle 24 and closure cap 28 during manufacture and seals nozzle 24 until initial use. During initial use, fracturable closure seal 26 is broken or fractured as illustrated in FIG. 8. Breaking of fracturable closure seal 26 also results in breaking of closure cap 28 away from nozzle 24 since closure cap 28 is formed integrally with fracturable closure seal 26. Tether 30, an elongated pliable material formed from the same material as the remainder of syringe 10, connects closure cap 28 to finger gripping part 16 of the hollow body. More specifically, tether 30 connects closure cap 28 to hollow body top 23 to prevent dislocation of closure cap 28 from the rest of syringe 10 and ultimately prevent loss of closure cap 28. Thus, accessibility of closure cap 28 is always maintained.

Referring to FIG. 9, use of syringe 10 is illustrated. During use, a user places his/her thumb through thumb ring 22. As previously described, thumb ring 22 is attached to closed rear wall 20 of pleated part 14. The user's fingers are then placed about the reduced cross sectional area 18 of finger gripping part 16. Shielding disc 32 prevents the user's fingers from coming into contact with nozzle 24. The shape of reduced cross-sectional area 18 is asymmetrical, thereby enhancing gripping of the syringe. Once fracturable closure seal 26 (see FIG. 8) has been broken, closure cap 28, having a frusto-conical inner shape, is placed over projection 34 (not shown), having a mating frusto-conical shape, located on shielding disc 32 to maintain closure cap 28 away from the open smaller end 24b of nozzle 24 during use of the syringe. The user then compresses the closed rear wall 20 using his/her thumb located in thumb ring 22 towards finger gripping part 16. As previously described, tether 30 connects closure cap 28 to finger gripping part 16 to prevent dislocation of closure cap 28 from the rest of syringe 10 in the event that closure cap 28 is accidentally removed from projection 34. Thus, accessibility of cap 28 is maintained.

Referring to FIG. 10, a cross-sectional view of closure cap 28 located on projection 34 looking in the direction of arrow 10 of FIG. 9 is illustrated. Projection 34 is located on shielding disc 32 which has hollow body top 23 on one side and a part of reduced cross-sectional area 18 on the other side. Projection 34 is hollow thereby allowing projection 34 to communicate with the interior 16a of finger gripping part 16 to provide additional volume for holding the contents of syringe 10. Projection 34 has an outer frusto-conical shape to receive closure cap 28 which has a mating frusto-conically shaped interior 36. Outwardly extending flange 38 which surrounds closure cap 28 facilitates manually grasping the closure cap and removal of closure cap 28 from projection 34.

Referring to FIG. 11, syringe 10 during non-use is illustrated. In particular, closure cap 28 is located on nozzle 24 while the syringe is not in use. Tether 30 connected to closure cap 28 and hollow body top 23 of finger gripping part 16 prevents dislocation of closure cap 28 from the rest of the syringe in the event closure cap 28 is removed from nozzle 24. Projection 34, in addition to being used for receiving closure cap 28 thereon while the syringe is in use, serves as an abutment to prevent the syringe from rolling along a surface during periods of non-use. In the embodiment illustrated in FIG. 11, two projections 34 are illustrated. Projections 34 are located on opposite sides of finger gripping part 16 of hollow body 12 thereby preventing the syringe from rolling along a surface more than a distance equal to approximately one-half the largest circumference of hollow body 12.

Referring to FIG. 12, a cross-sectional view of nozzle 24 looking in the direction of arrow 12 of FIG. 11 is illustrated. More specifically, nozzle 24 having closure cap 28 displaced thereon is shown. Nozzle 24 is frusto-conically shaped to receive closure cap 28 which has a mating frusto-conically shaped interior 36. Flange 38 of closure cap 28 enhances handling of closure cap 28 and removal of cap 28 from nozzle 24. Tether 30, which connects closure cap 28 to finger gripping part 16 (not shown), is connected to flange 38. It will be understood by those having skill in the art that tether 30 can be connected to any portion of closure cap 28.

Referring to FIG. 13, an alternative embodiment of the present invention is illustrated. The same reference numerals will be used for the same parts as already described with the prime notation added thereto. The alternative embodiment of syringe 10' according to the present invention has only one projection 34' extending laterally outward from shielding disc 32' of finger gripping part 16'. In this single projection embodiment, projection 34' functions in the same manner as previously described with respect to the multiple projection embodiment with the exception that the single projection embodiment prevents syringe 10' from rolling along a surface a distance approximately equal to the circumference of syringe 10' rather than a distance approximately equal to one-half the circumference of syringe 10.

Syringe 10 and 10' are manufactured using an automatic liquid packaging or form filled seal operation. The syringe is blow filled and sealed such that the finished syringe product is a sterile product, and there is no need for terminal sterilization of the syringe since it is manufactured in a sterile environment. The entire syringe 10, 10', including tether 30, 30' are formed by blowing a hollow hot body or parison of plastic through a blow nozzle into a closed mold and also dispensing a sterile solution through a fill nozzle into the same mold. Once the syringe is filled, the fill nozzle is retracted, and a seal mold comes across the top or bottom of the product. It will be understood by those having skill in the art that the solution may be a sterile or non-sterile solution. The solution helps to cool the hot plastic during manufacture. Thus, the process for manufacturing the syringe is molding the syringe by blowing a hollow hot plastic through a blow nozzle, filling the syringe with a solution through a fill nozzle injected into the mold, and sealing the top or bottom of the syringe. Therefore, when the mold is opened, a completely sealed, sterile syringe may be removed. The automatic liquid packaging equipment used to manufacture the syringe is readily available from Automatic Liquid Packaging, Inc. of Illinois.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed is:

1. A one piece molded syringe comprising:
a hollow body having a longitudinal axis and a closed rear wall, a pleated portion forming a substantial portion of said body and adjoining said closed rear wall, and a forward portion adjoining said pleated portion and having a reduced cross-sectional area providing a finger gripping area of the syringe;
thumb engageable means formed integrally with the closed rear wall of said hollow body for facilitating handling of the syringe during use;
a nozzle connected to and extending outwardly from the forward portion of said hollow body and communicating with the interior of the hollow body for discharging contents of the hollow body therethrough;
fracturable closure means formed integrally with the outer end of said nozzle for closing the nozzle until initial use;
a closure cap connected to said forward portion of said hollow body and adapted for closure of said nozzle when the nozzle is opened, and
projecting means, dimensioned to receive said closure cap thereon when the syringe is in use, extending laterally outward from the forward portion of said hollow body and beyond the periphery thereof and along an axis intersecting the longitudinal axis of said hollow body to also serve as an abutment for prevent rolling of the syringe along a surface.

2. A syringe as defined in claim 1 wherein said closure cap is formed integrally with said fracturable closure means and extends forwardly therefrom.

3. A syringe as defined in claim 1 wherein said projecting means comprises a pair of projections extending laterally outward from opposite sides of the forward portion of said hollow body.

4. A syringe as defined in claim 1 wherein said lateral projecting means is hollow and communicates with the interior of said hollow body.

5. A syringe as defined in claim 1 wherein said projecting means is frusto-conically shaped.

6. A syringe as defined in claim 5 wherein said closure cap has a mating frusto-conical inner shape to engage said frusto-conically shaped projecting means.

7. A syringe as defined in claim 1 wherein said closure cap has an outwardly extending flange surrounding the closure cap for facilitating manually grasping the closure cap and handling thereof.

8. A syringe as defined in claim 1 further comprising a tether connected to said closure cap and said forward portion of said body to connect said closure cap to said body and to prevent dislocation of the closure cap.

9. A one piece molded syringe comprising:
a hollow body having a longitudinal axis and a closed rear wall, a pleated portion forming a substantial portion of said body and adjoining said closed rear wall, and a forward portion adjoining said pleated portion and having a reduced cross sectional area providing a finger gripping area of the syringe;
thumb engageable means formed integrally with the closed rear wall of said hollow body for facilitating handling of said syringe during use;
a nozzle connected to and extending outwardly from the forward portion of said hollow body and communicating with the interior of the hollow body for discharging contents of the hollow body therethrough;
fracturable closure means formed integrally with the outer end of said nozzle for closing the nozzle until initial use;
a closure cap connected to said forward portion of said hollow body and adapted for closure of said nozzle when said nozzle is opened, wherein said closure cap is formed integrally with said fracturable closure means and extends forwardly therefrom; and
projecting means, dimensioned to receive said closure cap thereon when the syringe is in use, extending laterally outward from the forward portion of said hollow body and beyond the periphery thereof and along an axis intersecting the longitudinal axis of said hollow body to also serve as an abutment for preventing rolling of the syringe along a surface.

10. A syringe as defined in claim 9 wherein said projecting means comprises a pair of projections extending laterally outward from opposite sides of the forward portion of said hollow body.

11. A syringe as defined in claim 9 wherein said projecting means is hollow and communicates with the interior of said hollow body.

12. A syringe as defined in claim 9 wherein said projecting means is frusto-conically shaped.

13. A syringe as defined in claim 12 wherein said closure cap has a mating frusto-conical inner shape to engage said frusto-conically shaped projecting means.

14. A syringe as defined in claim 9 wherein said closure cap has an outwardly extending flange surrounding the closure cap for facilitating manually grasping the closure cap and handling thereof.

15. A syringe as defined in claim 9 further comprising a tether connected to said closure cap and said forward portion of said body to connect said closure cap to said body and to prevent dislocation of the closure cap.

16. A one piece molded syringe comprising:
a hollow body having a longitudinal axis and a closed rear wall, a pleated portion forming a substantial portion of said body and adjoining said closed rear wall, and a forward portion adjoining said pleated portion and having a reduced cross sectional area providing a finger gripping area of the syringe;
thumb engageable means formed integrally with the closed rear wall of said hollow body for facilitating handling of said syringe during use;
a nozzle connected to and extending outwardly from the forward portion of said hollow body and communicating with the interior of the hollow body for discharging contents of the hollow body therethrough;
fracturable closure means formed integrally with the outer end of said nozzle for closing the nozzle until initial use;

a closure cap dimensioned for closure of said nozzle when said nozzle is opened by fracturing of said fracturable closure means from said nozzle;

elongate pliable tethering means, connected to said closure cap and said hollow body, for connecting said closure cap to said hollow body to prevent dislocation of the closure cap; and projecting means dimensioned to receive said closure cap thereon extending laterally outward from the forward portion of said hollow body and beyond the periphery thereof and along an axis intersecting the longitudinal axis of said hollow body to serve as an abutment for preventing rolling of the syringe along a surface when the syringe is not in use and for receiving said closure cap thereon when said syringe is in use.

17. A syringe as defined in claim 16 wherein said projecting means comprises a pair of projections extending laterally outward from opposite sides of the forward portion of said hollow body.

* * * * *